United States Patent [19]

Finke et al.

[11] 4,052,486

[45] Oct. 4, 1977

[54] PROCESS FOR PREPARING CYCLIC PHOSPHINIC ACID ESTERS

[75] Inventors: Manfred Finke, Fischbach, Taunus; Hans-Jerg Kleiner, Kronberg, Taunus, both of Germany

[73] Assignee: Hoechst Aktiengesellschaft, Frankfurt am Main, Germany

[21] Appl. No.: 670,745

[22] Filed: Mar. 26, 1976

Related U.S. Application Data

[63] Continuation-in-part of Ser. No. 534,277, Dec. 19, 1974, abandoned.

[30] Foreign Application Priority Data

Apr. 5, 1975 Germany .............................. 2514871

[51] Int. Cl.² ............................................. C07F 9/15
[52] U.S. Cl. ..................................... 260/970; 260/936
[58] Field of Search .......................................... 260/970

[56] References Cited
FOREIGN PATENT DOCUMENTS 823,766    6/1975    Belgium

*Primary Examiner*—Anton H. Sutto
*Attorney, Agent, or Firm*—Curtis, Morris & Safford

[57] ABSTRACT

Process for preparing cyclic phosphinic acid esters of the formula (I)

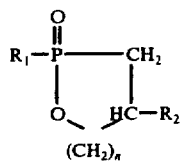

(I),

-continued

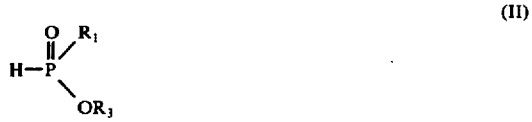

wherein $R_1$ is an alkyl radical having up to 18 carbon atoms or a phenyl radical being optionally substituted by alkyl, halogen or alkylated amino groups, $R_2$ stands for a hydrogen atom or has the same meaning as $R_1$ and $n$ is 1 or 2, which comprises reacting phosphinic acid monoesters of the formula (II)

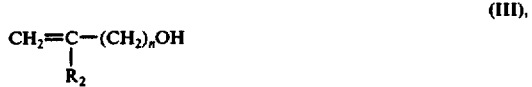

(II)

wherein $R_3$ is an alkyl radical having up to 8 carbon atoms optionally substituted by chlorine atoms and $R_1$ has the meaning given above, with an alkenol of the formula (III)

$$CH_2=C-(CH_2)_nOH$$
$$\quad\quad |$$
$$\quad\quad R_2$$
(III), wherein $R_2$ and $n$ have the aforesaid meaning, in the presence of catalytic quantities of free radical forming agents, splitting off the alcohol of formula (IV)

$R_3OH$ (IV)

simultaneously or subsequently and separating the reaction products, preferably by distillation.

13 Claims, No Drawings

PROCESS FOR PREPARING CYCLIC PHOSPHINIC ACID ESTERS

This application is a continuation-in-part application of Application Ser. No. 534,277, filed 12/19/74, now abandoned, U.S. Pat. No. 2,916,510 describes the preparation of cyclic phosphinic acid esters by reacting ethane phosphonous acid diethyl esters with 1,3-dibromopropane according to the following equation:

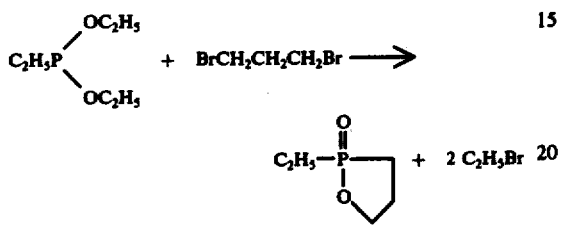

ps 2-Oxo1,2-oxa-phospholanes, also known as phostones in the literature, are obtained by this process in a maximum yield of 40%.

It is moreover known that 3-hydroxypropyl-phenyl-phosphinic acid cyclizes by splitting off water when heating it to a temperature of from 100° to 150° C giving phostones (cf. U.S. Pat. No. 2,648,695):

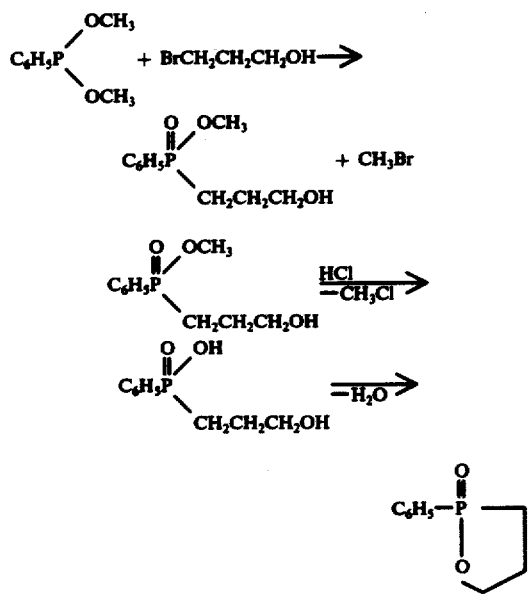

3-hydroxypropyl phenyl phosphinic acid consequently is obtained by an Arbuzow rearrangement of benzene phosphonous acid dimethyl ester with 3-bromopropanol and by subsequent saponification of the intermediately formed 3-hydroxypropyl phenyl phosphinic acid methyl ester. There are no data about the yields in said process.

It has now been found that cyclic phosphinic acid esters of the formula (I)

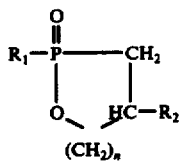

(I),

wherein $R_1$ stands for an alkyl radical having up to 18 carbon atoms, preferably up to 12, especially up to 6 carbon atoms or a phenyl radical being optionally substituted by alkyl, halogen or alkylated amino groups, $R_2$ is a hydrogen atom or has the same meaning as $R_1$ and $n$ is 1 or 2, can be prepared by reacting phosphinic acid monoesters of the formula (II)

(II)

wherein $R_3$ stands for an alkyl radical optionally substituted by chlorine atoms, preferably singly substituted and having up to 8 carbon atoms, preferably up to 4 carbon atoms and $R_1$ has the aforesaid meaning, with an alkenol of the formula (III), (III),

wherein $R_2$ and $n$ have the aforesaid meaning, in the presence of catalytic quantities of free radical forming agents, by splitting off the alcohol of formula (IV)

$$R_3OH \qquad (IV)$$

simultaneously or subsequently and by separating the reaction products, preferably by distillation.

It is surprising that the reaction of phosphinic acid monoesters of formula (II) with an alkenol of formula (III) according to the process of the invention runs quickly and smoothly and gives cyclic phosphinic acid esters in high yields.

Alkenols of formula (III) with $n = 1$ yield five-membered cyclic phosphinic acid esters, also called 2-oxo-1,2-oxaphospholanes, while alkenols of formula (III) in which $n$ is 2 give six-membered cyclic phosphinic acid esters also called 2-oxo-1,2-oxaphosphorinanes. 2-oxo-1,2-oxaphospholanes as well as 2-oxo-1,2-oxaphosphorinanes are quite generally denominated phostones.

As compared therewith the free radical initiated addition of phosphorous acid diesters to allyl alcohols only leads to the corresponding 3-hydroxypropyl phosphonic acid dialkyl esters in a moderate yield(cf. U.S. Pat. No. 2,724,718).

It is furthermore surprising that the intermediately occurring 3-hydroxypropyl or 4-hydroxybutyl phosphinic acid esters immediately cyclize giving phostones while splitting off alcohols. It is not necessary therefore to cleave the 3-hydroxypropyl phosphinic acid esters as described in U.S. Pat. No. 2,648,695 with concentrated hydrogen chloride and to transform subsequently the 3-hydroxypropyl phosphinic acids formed into the phostones by splitting off water. The fact that aforesaid reaction steps may be dispensed with constitutes considerable technical progress.

The phosphinic acid monoesters of formula (II) used as starting materials may be easily obtained by known processes from dichlorophosphines and an excess of alcohol.

Compared to phosphonous acid diesters used as starting material, for example, in U.S. Pat. Nos. 2,916,510 and 2,648,695 the phosphinic acid monoesters of formula (II) may also be prepared from dichlorophosphines in the absence of tertiary amines.

Examples of suitable phosphinic acid monoesters of formula (II) are methane phosphinic acid monomethyl esters, monoethyl esters, monopropyl esters, monoisopropyl esters, monobutyl esters, monoisobutyl esters, monooctyl esters, ethane phosphinic acid monomethyl esters, monoethyl esters, monobutyl esters, propane phosphinic acid monobutyl esters, hexane phosphinic acid monoisobutyl esters, dodecane hosphinic acid monopropyl esters, octadecane phosphinic acid monisobutyl esters, benzene phosphinic acid monobutyl esters, chlorobenzene phoshinic acidmonoisobutyl esters and dimethylaminobenzene phosphinic acid monoisobutyl esters.

Suitabe alkenols of formula (III), wherein $n$ is 1, are, for example, allyl alcohol as well as substituted allyl alcohols, such as 2-methyl allyl alcohol, 2-ethyl allyl alcohol, 2-butyl allyl alcohol, 2-hexyl allyl alcohol, 2-dodecyl allyl alcohol, 2-hexadecyl allyl alcohol, 2-phenyl allyl alcohol, 2-chlorophenyl allyl alcohol, 2-dimethylaminophenyl allyl alcohol, or 2-diethylaminophenyl allyl alcohol. The preferred compound is allyl alcohol.

Suitable alkenols of formula (III), wherein $n$ is 2, are, for example, buten-1-ol-4, 2-methyl-buten-1-ol-4, 2-ethyl-buten-1-ol-4, 2-butyl-buten-1-ol-4, 2-hexyl-buten-1-ol-4, 2-dodecylbuten-1-ol-4, 2-hexadecyl-buten-1-ol-4, 2-phenyl-buten-1-ol-4, 2-chorophenyl-buten-1-ol-4, 2-dimethylaminophenyl-buten-1-ol-4 or 2-diethylaminophenyl-buten-1-ol-4. Preferred compounds are buten-1 -ol-4 and 2-methylbuten-1-ol-4.

All known free radical forming agents may be used for the free radical initiation of the addition reaction according to the invention provided that they decompose to a satisfactory extent into free radical components or are capable of forming free radical compoundsunder the reaction conditions. Examples of suitable free radical forming agents are, consequently, peroxides or other free radical forming agents such as ditertiary butylperoxide, tertiary butylperbenzoate, tertiary butyl-cumylperoxide, 2,5-dimethylhexane-bis-2,5-(peroxybenzoate), tertiary butylhydroperoxide, bis-2,2-(tertiary butylperoxy)-butane, acetyl enzoylperoxide, dicumylperoxide, or azobisisobutanol diacetate. The free radical forming agents generally are used in catalytic quantities of about 0.1 to 2 mol %, preferably from .5 to 1 mol %, calculated on the phosphinic cid onoester of formula (II), they are advantageously added to said ester while being mixed with the alkenol, optionally while using an inert slvent. The reaction according to the invention may also be initiated by radiation. The process according to the invention is generally carried out as follows: Approximately the 1- to 1.5-fold molar quantity of an alkenol of formula (III) mixed with 0.1 to 2 mol %, preferably 0.5 to 1 mol %, of a free radical forming agent is added gradually, while stirring, to a phosphinic acid monoester of formula (II) at a temperature interval of from 100° to 190° C, preferably from 130° to 170° C, optionally while using an inert solvent. The phosphinic acid monoester of formula (II) and the alkenol component of formula (III) are advantageously used in this process in a molar proportion of about 1 : 1. It is likewise possible to use an excess of one of the reactants, although this generally is of no advantage when using free radical forming agents. However, if the solubility of the free radical forming agent in the alkenol component is unsatisfactory, the alkenol component may be used in an excess greater than the 1.5 fold molar quantity, whereby it is possible to recover the excess after the reaction is terminated. Instead of an increased excess of alkenol component other inert solvents may be added to the mixture of reactants as dissolving intermediaries or as diluents, for example aliphatic, cycloaliphatic, aromatic, or araliphatic hydrocarbons which are optionally substituted, such as xylene, chlorobenzene, chlorotoluene, dichlorobenzene, tetralene, decalene, dodecyl benzene, higher boiling gasoline fractions; acid amides such as dimethyl formamide or hexamethyl phosphorous acid triamide; ethers such as dialkyl ethers of ethylene glycol or of polyethylene glycol, or of propylene glycol, or of polypropylene glycol, and dimethyl sulfoxide. Inert solvents having a boiling point greater than that of the reaction product may advantageously rest in the bottom product of the fractionated distillation of the reaction mixture. The process according to the invention is, however, carried out advantageously in the absence of inert solvents.

The alcohol $R_3OH$ formed in the cyclization of the 3-hydroxypropyl or 4-hydroxybutyl phosphinic acid ester is continuously distilled off from the reaction mixture over a column in the foresaid process. It is also possible to split off the acohol $R_3OH$ by distillation, when the reaction is finished, especially in the case of a rather long chain radical $R_3OH$, the temperature range of the cleavage of the alcohol being identical with that of the process for the addition of the alkenol.

A nitrogen or inert gas atmosphere generally is not required for carrying out the reaction, but may improve the yield in the case of short chain phosphinic acid mnoesters.

The reaction time in the process according to the invention generally ranges from about 2 to 6 hours. The phostones may be easily separated by fractionated distillation from the alcohols $R_3OH$ and possibly un-reacted starting materials as well as from optionally present inert solvents.

It is recommended that the material to be distilled be fractionated repeatedly in order to obtain pure phostones, since small portions of the alcohol $R_3OH$ are formed in the distillation. The yields of phostones range from 75 to 90% of the theoretical yield, calculated on the phosphinic acid monoalkyl ester used.

The 2-oxo-1,2-oxaphospholanes and the 2-oxo-1,2-oxaphosphorinanes of formula (I) prepared by the process according to the invention are valuable intermediates for fire-retarding paints and may be used as flame-resistant additives for lubricants.

The following examples illustrate the invention.

EXAMPLE 1

Preparation of 2-oxo-2-methyl-1,2-oxaphospholane 320 g (5.5 mols) of allyl alcohol containing 5 g (0.025 mol) of tertiary butylperbenzoate were introduced dropwise within 3 hours into 680 g (5 mols) of methane phosphinic acid monoisobutyl ester at a temperature of from 145° to 150° C. After about 2.5 hours the splitting off of isobutyl alcohol started, which alcohol was then drawn off from the reaction mixture by distillation over a Vigreux column. The crude product was then distilled by fractionation under reduced pressure. 560 g of phospholane were obtained at a boiling point of from 95° to 97° C under 0.2 mm Hg which corresponds to a yield of 93% of the theoretical yield.

EXAMPLE 2

Preparation of 2-oxo-2-methyl-b 1,2-oxaphospholane

A mixture of 35 g (0.6 mol) of allyl alcohol and 1 g of di-tertiary butylperoxide (0.007 mol) was introduced dropwise into 68 g (0.5 mol) of methane phosphinic acid monoisobutyl ester at a temperature of from 160° to 170° C.

Isobutanol and the excess of allyl alcohol were distilled off from the reaction mixture over a short Vigreux column. When the addition was finished (after about 2 hours), the residue was distilled roughly under reduced pressure and fractionated subsequently. 50 g of phospholane were obtained (boiling point of from 99° to 100° C under 0.4 mm Hg), which corresponds to a yield of 84% of the theoretical yield.

EXAMPLE 3

Preparation of 2-oxo-2-2-methyl-1,2-oxaphospholane 25 g (0.43 mol) of allyl alcohol containing 0.5 g of di-tertiary butylperoxide (0.0035 mol) were slowly introduced dropwise into 43 g (0.35 mol) of methane phosphinic acid mono-isopropyl ester at a temperature of from 150° to 170° C. The isopropanol formed was distilled off from the reaction mixture simultaneously. 31 g of phospholane were obtained therefrom after distillation under reduced pressure (boiling point of from 90° to 92° C under 0.1 mm Hg), which corresponds to a yield of 74% of the theoretical yield.

EXAMPLE 4

Preparation of 2-oxo-2,4-dimethyl-1,21-oxaphospholane

A mixture of 45 g (0.62 mol) of 2-methyl allyl alcohol and 1 (0.007 mol) of di-tertiary butylperoxide were introduced dropwise into 68 g (0.5 mol) of methane phosphinic acid mono-isobutyl ester at a emperature of from 160° to 170° C. Isobutanol and 2-methyl allyl alcohol were simultaneously distilled off from the reaction mixture over a short Vigreux column. 52 g of phospholane (boiling point of from 108° to 110° C under 0.2 mm Hg) were obtained after distillation of the reaction product in vacuo, which corresponds to a yield of 78% of the theoretical yield.

EXAMPLE 5

Preparation of 2-oxo-2-phenyl-1,2-oxaphospholane 27 g (0.47 mol) of allyl alcohol containing 0.5 g (0.0035 mol) of di- tertiary butyl peroxide were introduced dropwise into 80 g (0.4 mol) of benzene phosphinic acid monobutyl ester within 1.5 hours at a temperature of 160° C. Thereafter, the excess of allyl alcohol and n-butanol were distilled off in a water jet vacuum at a temperature of from 160° to 170° C. The residue was fractionated in a high vacum. 57 g (77% of the theoretical yield) of 2-oxo-2-phenyl-1,2-oxaphospholane distilled over at a temperature of from 146° to 148° C.

EXAMPLE 6

Preparation of 2-oxo-2-methyl-1,2-oxaphosphorinane 151 g of methane phosphinic acid isobutyl ester were heated to 160°- 170° C in a nitrogen atmosphere and, while vigorously stirring, a mixture of 80 g of buten-1-ol-4 and 0.8 g di-tert-butyl peroxide was added dropwise, while isobutanol distilled off over a short column. The reaction mixture was then distilled. 72 g of 2-oxo-2-methyl-1,2-oxo-phosphorinane boiling at 82°0 C under 0.2 mm Hg were obtained, corresponding to a yield of about 50% of the theoretical yield. In addition, 68 g of a higher boiling fraction were obtained which was found to be 4-hydroxybutyl-methylphosphinic acid isobutyl ester boiling at 155° –160° C under 0.2 mm Hg, corresponding to a yield of 30% of the theoretical yield. The latter product can be readily transformed into 2-oxo-2-methyl-1,2-oxaphosphorinane by known methods, for example as described in U.S. Pat. No 2,648,695.

EXAMPLE 7

Preparation of 2-oxo-2,4-dimethyl-1,2-oxaphosphorinane 316 g of methane phosphinic acid isobutyl ester were heated to 160° C in a nitrogen atmosphere and, while vigorously stirring, a mixture of 200 g of 2-methylbuten-1-ol-4 and 2 g di-tert-butyl peroxide was dropped in. During the course of the reaction the temperature rose to 175° C and isobutanol distilled off over a short column. The reaction mixture was then distilled. The 2-oxo-2,4-dimethyl-1,2-oxa-phosphorinane was obtained in the form of two position isomers, i.e. isomer I and isomer II. 167 g of isomer I boiling at 83° C under 0.2 mm Hg, corresponding to a yield of 49% of the theoretical yield, and 105 g of isomer II boiling at 105° C under 0.2 mm Hg and melting at 78° –83° C, corresponding to a yield of 31% of the theoretical yield, were obtaine d, the total yield thus being 80% of the theoretical yield.

We claim:

1. A process for preparing a cyclic phosphinic acid ester of the formula

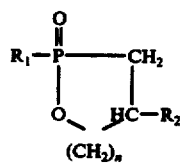

wherein $R_1$ is an alkyl of up to 18 carbon atoms, phenyl or phenyl substituted by alkyl, halogen or alkylated amino, $R_2$ is hydrogen or has the same meaning as $R_1$ and $n$ is 1 or 2, which comprises reacting a phosphinic acid monoester of the formula

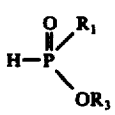

wherein $R_3$ is an alkyl of up to 8 carbon atoms, or an alkyl of up to 8 carbon atoms substituted by chlorine, with an alkenol of the formula

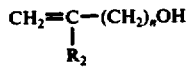

in the presence of a catalytic quantity of a free radical forming agent at a temperature of from 100° C to 190° C.

2. The process as defined in claim 1, wherein $n$ is 1.

3. The process as defined in claim 1, wherein $R_1$ is an alkyl of up to 6 carbon atoms.

4. The process as defined in claim 1, wherein $R_3$ is alkyl or chloroalkyl of up 4 carbon atoms.

5. The process as defined in claim 1, wherein $R_3$ is monochloro alkyl.

6. The process as defined in claim 1, wherein the amounts of phosphinic acid monoester and alkenol are in a molar proportion of from 1 : 1 to 1 : 1.5.

7. The process as defined in claim 1, wherein the catalytic quantity of the free radical forming agent is from 0.1 to 2 1 mol %, calculated on the phosphinic acid monoester.

8. The process as fined in claim 1, wherein the reaction is carried out at a temperature of from 130° to 170° C.

9. The process as defined in claim 1, wherein the free radical forming agent is di-tertiary butylperoxide or tertiary butylperbenzoate.

10. The process as defined in claim 1, wherein the alkenol is allyl alcohol, buten-1-ol-4 or 2-methylbuten-1-ol-4.

11. The process as defined in claim 1, wherein the reaction occurs in an inert solvent.

12. The process as defined in claim 1, wherein the reaction occurs in an inert gas atmosphere.

13. The process as defined in claim 1, wherein the reaction products are separated by distillation.